United States Patent
Kelly et al.

(10) Patent No.: US 8,124,735 B2
(45) Date of Patent: Feb. 28, 2012

(54) POROUS KERATIN CONSTRUCT AND METHOD OF MAKING THE SAME

(75) Inventors: Robert James Kelly, Christchurch (NZ); Clive Marsh, Christchurch (NZ); Mohammad Azam Ali, Christchurch (NZ); Gudmunder Fertram Sigurjonsson, Christchurch (NZ)

(73) Assignee: Keraplast Technologies, Ltd., San Antonio, TX (US)

( * ) Notice: Subject to any disclaimer, the term of this patent is extended or adjusted under 35 U.S.C. 154(b) by 15 days.

(21) Appl. No.: 12/000,222

(22) Filed: Dec. 11, 2007
(Under 37 CFR 1.47)

(65) Prior Publication Data

US 2009/0105456 A1    Apr. 23, 2009

Related U.S. Application Data

(60) Provisional application No. 60/874,010, filed on Dec. 11, 2006, provisional application No. 60/924,032, filed on Apr. 27, 2007.

(51) Int. Cl.
A61K 38/17    (2006.01)
(52) U.S. Cl. ....................................... 530/357
(58) Field of Classification Search ................... 530/357
See application file for complete search history.

(56) References Cited

U.S. PATENT DOCUMENTS

| | | | |
|---|---|---|---|
| 2,591,945 A | 4/1952 | Koerner et al. | |
| 3,567,363 A | 3/1971 | Wolfram | |
| 3,619,116 A | 11/1971 | Saville | |
| 3,642,498 A * | 2/1972 | Anker | 426/302 |
| 3,644,084 A | 2/1972 | Hsiung et al. | |
| 3,883,647 A | 5/1975 | Geller | |
| 4,135,942 A | 1/1979 | Kikkawa | |
| 4,172,073 A | 10/1979 | Kadri et al. | |
| 4,407,793 A | 10/1983 | Akimora et al. | |
| 4,775,620 A | 10/1988 | Cardiff et al. | |
| 4,895,722 A | 1/1990 | Abe et al. | |
| 4,904,602 A | 2/1990 | Pigiet et al. | |
| 4,948,876 A | 8/1990 | Bore et al. | |
| 4,969,880 A | 11/1990 | Zamierowski | |
| 5,071,441 A | 12/1991 | Schnetzinger et al. | |
| 5,154,916 A | 10/1992 | Arraudeau et al. | |
| 5,358,935 A | 10/1994 | Smith et al. | |
| 5,460,967 A | 10/1995 | Fink | |
| 5,602,094 A | 2/1997 | Goddard | |
| 5,763,583 A | 6/1998 | Arai et al. | |
| 5,830,481 A | 11/1998 | Cauwet-Martin et al. | |
| 5,932,552 A | 8/1999 | Blanchard et al. | |
| 5,972,385 A | 10/1999 | Liu et al. | |
| 6,039,962 A | 3/2000 | Cauwet-Martin et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,203,574 B1 | 3/2001 | Kawamura | |
| 6,312,674 B1 | 11/2001 | Maubru et al. | |
| 6,432,435 B1 | 8/2002 | Timmons et al. | |
| 6,514,744 B2 | 2/2003 | Murata et al. | |
| 6,544,548 B1 | 4/2003 | Siller-Jackson | |
| 6,783,546 B2 | 8/2004 | Zucherman | |
| 6,846,940 B2 | 1/2005 | Gaetani et al. | |
| 7,169,896 B2 | 1/2007 | Schrooyen et al. | |
| 2001/0018614 A1 | 8/2001 | Bianchi | |
| 2002/0004068 A1 | 1/2002 | DiDrusco | |
| 2002/0013408 A1 | 1/2002 | Rhee | |
| 2002/0035046 A1 | 3/2002 | Lukenbach et al. | |
| 2002/0183858 A1 | 12/2002 | Contiliano et al. | |
| 2003/0035820 A1 | 2/2003 | Timmons et al. | |
| 2003/0039676 A1 | 2/2003 | Boyce et al. | |
| 2005/0232963 A1* | 10/2005 | Peplow et al. | 424/423 |
| 2006/0165635 A1 | 7/2006 | Kelly et al. | |
| 2006/0205652 A1 | 9/2006 | Zamora et al. | |

FOREIGN PATENT DOCUMENTS

| | | |
|---|---|---|
| CN | 1403643 | 3/2003 |
| CN | 1425813 | 6/2003 |
| EP | 0 628 573 A1 | 12/1994 |
| EP | 1 201 736 B1 | 4/2005 |
| FR | 1503640 | 12/1967 |
| FR | 2687577 A1 | 8/1993 |
| GB | 2 115 427 | 9/1983 |
| JP | 53-119900 | 10/1978 |
| JP | 63-301809 | 12/1988 |
| JP | 03-007596 | 1/1991 |
| JP | 03-294297 | 12/1991 |
| JP | 05-222100 | 8/1993 |
| JP | 05-320358 | 12/1993 |
| JP | 06-100600 | 4/1994 |
| JP | 06-220713 | 8/1994 |
| JP | 06 192433 | 12/1994 |
| WO | WO 92/02238 | 2/1992 |

(Continued)

OTHER PUBLICATIONS

"Mils to Millimeter Conversion", obtained from www.reade.com/Conversion/mils_to_%2Omm.html—printed Dec. 28, 2009.*

Maclaren, John A., et al., "Wool Science the Chemical Reactivity of the Wool Fibre", pp. 12-14, 1981.

Hunter, Emma A.L., et al., "Cysteine and Methionin Supplementation Modulate the Effect of Tumor Necrosis Factor a on Protein Synthesis, Glutathione and Zinc Concentration of Liver and Lung in Rats Fed a Low Protein Diet", American Institute of Nutrition, vol. 124, No. 12, pp. 2319-2328, 1994.

Homandberg, G.A., et al., "Fibronectin Fragment Mediated Cartilage Chondrolysis. I. Suppression by Anti-Oxidants", Biochemica et Biophysica Acta, vol. 1317, pp. 134-142, 1996.

(Continued)

Primary Examiner — Suzanne M Noakes
(74) Attorney, Agent, or Firm — Vinson & Elkins LLP

(57) ABSTRACT

The invention relates to a porous keratin construct material comprising keratin protein for use in wound healing applications. The porous keratin construct is capable of bio-absorbing into a wound to promote wound healing. The rate at which the construct bio-absorbs into the wound may be controlled altered by controlling the degree of disulfide cross-linking between the keratin proteins in the porous keratin construct. The invention is also related to a method of making the porous keratin construct.

11 Claims, 1 Drawing Sheet

FOREIGN PATENT DOCUMENTS

| WO | WO 98/51265 | 11/1998 |
|---|---|---|
| WO | WO 99/18922 | 4/1999 |
| WO | WO 99/19005 | 4/1999 |
| WO | WO 99/26570 | 6/1999 |
| WO | WO 00/23039 | 4/2000 |
| WO | WO 00/41739 | 7/2000 |
| WO | WO 00/70049 | 11/2000 |
| WO | WO 02/09659 | 2/2002 |
| WO | WO 03/011894 | 2/2002 |
| WO | WO 03/018673 | 3/2003 |
| WO | WO 03/103737 | 12/2003 |

OTHER PUBLICATIONS

Parcell, Stephen, "Sulphur in Human Nutrition and Applications in Medicine", Alternative Medicine Review, vol. 7, No. 1, pp. 22-44, 2002.

Zafarullah, M., et al., "Molecular Mechanisms of N-Acetylcysteine Actions", Cellular and Molecular Life Sciences, vol. 60, No. 1, pp. 6-20, 2003.

Hummel, Klaus M., et al., "Cysteine Proteinase Cathepsin K mRNA Is Expressed in Synovium of Patients with Rheumatoid Arthritis and Is Detected at Sites of Synovial Bone Destruction", Journal of Rheumatology, vol. 25, No. 10, pp. 1887-1984, 1998.

Bradley, Helen, et al., "Sulfate Metabolism is Abnormal in Patients with Rheumatoid Arthiritis", Journal of Rheumatology, vol. 21, No. 7, pp. 1192-1196, 1994.

Wilkinson, L.J., et al., "Cysteine Diosygenase: Modulation of Expression in Human Cell Lines by Cytokines and Control of Sulphate Production", Toxicology in Vitro, vol. 16, pp. 481-483, 2002.

Tappaz, M.L., "Taurine Biosynthetic Enzymes and Taurine Transporter: Molecular Identification and Regulations", Neurochemical Research, vol. 29, No. 1, pp. 83-96, Jan. 2004.

Kontny, E., et al., "Impaired Generation of Taurine Chloramine by Synovial Fluid Neutrophils of Rheumatoid Arthritis Patients", Amino Acids, vol. 24, No. 4, pp. 415-418, 2002.

Roughley, Peter J., et al., "Cartilage Proteoglycans: Structure and Potential Functions", Microscopy Research and Technique, vol. 28, No. 5, pp. 385-397, 1994.

Rossi, Antonio, et al., "In Vitro Proteoglycan Sulfation Derived from Sulfhydryl Compounds in Sulfate Transporter Chondrodysplasias", Pediatric Pathology and Molecular Medicine, vol. 22, No. 4, pp. 311-321, 2003.

Kusche-Gullberg, Marion, et al., "Sulfotransferases in Glycosaminoglycan Biosynthesis", Current Opinion in Structural Biology, vol. 13, pp. 605-611, 2003.

Rath, Virginia L., "Sulfotransferase Structural Biology and Inhibitor Discovery", Drug Discovery Today, vol. 9, No. 23, pp. 1003-1011, Dec. 2004.

Venkatachalam, K.V., "Human 3'-phosphoadenosine 5'-phosphosulfate (PAPS) Synthase: Biochemistry. Molecular Biology and Genetic Deficiency", IUBMB Life, vol. 55, pp. 1-11, 2003.

Heyland, Daren K., et al., "Antioxidant Nutrients: A Systematic Review of Trace Elements and Vitamins in the Critically Ill Patient", Intensive Care Med., vol. 31, pp. 327-337, 2005.

Elsayed, Nabil M., "Antioxidant Mobilization in Response to Oxidative Stress: A Dynamic Environmental-Nutritional Interaction", Nutrition, vol. 17, pp. 828-834, 2001.

Serhan, Charles N., et al., "Resolution of Inflammation: The Beginning Programs the End", Nature Immunology, vol. 6, No. 12, pp. 1191-1197, Dec. 2005.

Henson, Peter M., "Dampening Inflammation", Nature Immunology, vol. 12, No. 12, pp. 1179-1182, Dec. 2005.

Verbruggen, G., "Chondroprotective Drugs in Degenerative Joint Diseases", Journal of Rheumatology, vol. 45, pp. 129-138, 2006.

Largo, R., et al., "Glucosomine Inhibits IL-1b-Induced NFkB Activation in Human Osteoarthritic Chondrocytes", OsteoArthritis and Cartilage, vol. 11, pp. 290-298, 2003.

Chan, P.S., et al., "Glucosamine and Chondroitin Sulfate Regulate Gene Expression and Synthesis of Nitric Oxide and Prostaglandin E2 in Articular Cartilage Explants", OsteArthritis and Cartilage, vol. 13, pp. 387-394, 2005.

Rassin, D.K., et al., "Nutritional Approaches to Improve Cognitive Development During Infancy: Antioxidant Compounds", Acta Paediatr Suppl., vol. 442, pp. 34-41, 2003.

Brugge, Karen L., et al., "The Role of Alterations in Free Radical Metabolism in Mediating Cognitive Impairments in Down's Syndrome", EXS, vol. 62, pp. 190-198, 1992.

Del Marmol, Veronique, et al., "Cysteine Deprivation Promotes Eumelanogenesis in Human Melanoma Cells", Journal of Investigative Dermatology, vol. 107, No. 5, pp. 698-702, 1996.

Smit, Nico P.M., et al., "Melanogenesis in Cultured Melanocytes Can Be Substantially Influenced by L-Tyrosine and L-Cysteine", Journal of Investigative Dermatology, vol. 109, No. 6, pp. 796-800, 1997.

Fujiwara, Y., et al., "Effect of Simultaneous Administration of Vitamin C, L-Cysteine and Vitamin E on the Melanogenesis", Biofactors, vol. 21, Nos. 104, pp. 415-418, 2004.

Kong, Kwang-Hoon, et al., "Expression and Characterization of Human Tyrosinase From a Bacterial Expression System", Comparative Biochemistry and Physiology, Part B, vol. 125, pp. 563-569, 2000.

Yamamura, Tatsuo, et al., "Antimelanogenic Activity of Hydrocoumarins in Cultured Normal Human Melanocytes by Stimulating Intracellular Glutathione Synthesis", Archives of Dermatological Research, vol. 294, No. 8, pp. 349-354m 2002.

Alonso, Laura C., et al., "Molecular Genetic and Endocrine Mechanisms of Hair Growth", Hormone Research, vol. 60, pp. 1-13, 2003.

Olney, J.W., et al., Brain Damage in Infant Mice Following Oral Intake of Glutamate, Aspartate or Cysteine, Nature, vol. 227, pp. 609-610, 1970.

Riise, G.C., "The Intrabronchial Microbial Flora in Chronic Bronchitis Patients: A Target for N-Acetylcysteine Therapy", European Respiratory Journal, vol. 7, pp. 94-101, 1994.

Grandjean, E.M., et al., "Efficacy of Oral Long-Term N-Acetylcysteine in Chronic Bronchopulmonary Disease: A Meta-Analysis of Published Double-Bline, Placebo-Controlled Clinical Trials", Clinical Therapy, vol. 22, pp. 209-221, 2000.

Hansen, N.C.G., et al., Orally Administered N-Acetylcysteine May Improve General Well-Being in Patients with Mild Chronic Bronchitis, Respitory Medicine, vol. 88, pp. 531-535, 1994.

Rasmussen, J.B., et al., Reduction in Days of Illness After Long-Term Treatment with N-Acetylcysteine Controlled-Release Tablets in Patients with Chronic Bronchitis, European Respitory Journal, vol. 1, pp. 351-355, 1988.

Parr, G.D., et al., Oral Fabrol (oral N-acetylcysteine) in Chronic Bronchitis, British Journal of Diseases of Chest, vol. 81, pp. 341-348, 1987.

Ardissino, D., et al., "Effect of Transdermal Nitroglycerin or N-acetylcysteine, or Both, in the Long-Term Treatment of Unstable Angina Pectoris", Journal of the American College of Caridiology, vol. 29, pp. 941-947, 1997.

Estensen, R.D., et al., "N-acetylcysteine Suppression of the Proliferative Index in the Colon of Patients with Previous Adenomatous Colonic Polyps", Cancer Letters, vol. 147, pp. 109-114, 1999.

Kinscherf, R., et al., Effect of glutathione Depletion and Oral N-acetylcysteine Treatment on CD4+ and CD8+ Cells. FASEB Journal, vol. 8, pp. 448-451, 1994.

Akerlund, et al., "Effect of N-acetylcystine (NAC) Treatment on HIV-1 Infection: A Double-Blind Placebo-Controlled Trial", European Journal of Clinical Pharmacology, vol. 50, pp. 457-461, 1996.

Zhang, Shumin, et al., "A Prospective Study of Plasma Total Cysteine and Risk of Breast Cancer", Epidemiology Biomarkers & Prevention, vol. 12, pp. 1188-1193, 2003.

James, L.P., et al., "Effect of N-Acetylcysteine on Acetaminophen Toxicity in Mice: Relationship to Reactive Nitrogen and Cytokine Formation", Toxicological Sciences, vol. 75, No. 2, pp. 458-467, 2003.

Shankar, K., et al., "Type 1 Diabetic Mice are Protected fro mAcetaminophen Hepatotoxicity", Toxicology Sciences, vol. 72, No. 2, pp. 220-234, 2003.

Goodman, M.T., Case-Control Study of Plasma Folate, Homocysteine, Vitamin B12, and Cysteine as Markers of Cervical Dysplasia, Cancer, vol. 89, No. 2, pp. 376-382, 2000.

Bernard, G.L. et al., "A Trial of Antioxidants N-Acetylcysteine and Procysteine in ARDS. The Antioxidant in ARDS Study Group", Chest, vol. 112, pp. 164-172, 1997.

Tepel, M., et al., "Prevention of Radiographic-Contrast-Agent-Induced Reductions in Renal Function by Acetylcysteine", New England Journal of Medicine, vol. 343, pp. 180-184, 2000.

Walters, M.T., et al., "A Double-Blind, Cross-Over, Study of Oral N-Acetylcysteine in Sjogren's Syndrome", Scand J. Rheumatol Suppl., vol. 61, pp. 253-258, 1986.

De Vries, N., et al., "N-acetyl-l-cysteine", Journal of Cellular Biochemistry Supplement, vol. 17F, pp. 270-277, 1993.

Beloqui, O., et al., "N-aceytl Cysteine Enhances the Response to Interferon-Alpha in Chronic Hepatitis C: A Pilot Study", Journal of Interferon Research, vol. 13, pp. 279-282, 1993.

Feghali, J.G., et al., "L-n-acetyl-cysteine Protection Against Cisplatin-Induced Auditory Neuronal and Hair Cell Toxicity", Laryngoscope, vol. 111, No. 7, pp. 1147-1155, 2001.

Balli, R., "Controlled Trial on the Use of Oral Acetylcysteine in the Treatment of Glue-Ear Following Drainage", European Journal of Respitory Diseases, vol. 61, Suppl. 111, pp. 159, 1980.

Yalcin, E. et al., "N-acetylcysteine in Chronic Blepharitis", Cornea, vol. 21, pp. 164-168, 2002.

De Flora, S., et al., "Mechanisms fo N-acetylcysteine in the Prevention of DNA Damage and Cancer, with Special Reference to Smoking-Related End-Points", Carcinogenesis, vol. 22, pp. 999-1013, 2001.

Connors, S.L., et al., "Secretin and Autism: The Role of Cysteine", Journal of the American Academy of Child and Adolescent Psychiatry, vol. 38, pp. 795-796, 1999.

Apple, S.K., et al., "Effect of Feather Meal on Live Animal Performance and Carcass Quality and Composition of Growing Finishign Swing", Journal of Animal Science, vol. 81, pp. 172-181, 2003.

Loy, T.W., et al., "Effects of Supplementation on Intake an Growth of Nursing Calves Grazing Native Range in Southeastern North Dakota", Journal of Animal Science, vol. 80, pp. 2717-2725, 2002.

Pohl, Thomas, "Concentration of Proteins and Removal of Solutes", Methods in Enzymology, vol. 182, pp. 68-83, 1990.

McNeil, Steven, "Heavy Metal Removal Using Wool Filters", Asian Textile Journal, pp. 88-90, May-Jun. 2001.

Fukatsu, K., "Degradation of Fe(III)—Wool Keratin Complex by Hydrogen Peroxide", Kumanoto Women's University, Kumamoto, Japan, Sen'i Gakkaishi (Fiber), vol. 46, No. 5. pp. 186-191 1990.

Thomas, Helga, et al., "In Vitro Reconstitution of Wool Intermediate Filaments", Int. J. Biol. Macromol., vol. 8, pp. 258-264, Oct. 1986.

Harrap, B.S., et al., "Soluble Derivatives of Feather Keratin", Biochem J., vol. 92, No. 8, pp. 8-18, 1964.

Swan, J.M., "The Reaction of Protein Thiol and Disulphide Groups with Cupric Sulphite Solutions", pp. 69-83, Sep. 1960.

Thomas, Helga, et al., "Experiments for the Isolation of Matrix Proteins of Wool in Disulphide Form", Melliand Textilberichte, pp. 297-300, Apr. 1983.

Goto M, Suyama K., "Occlusion of Transition Metal Ions by New Adsorbents Synthesized from Plant Polyphenois and Animal Fibrous Proteins", www.pubmed.gov, Dec. 18, 2006.

Mies, H.H., et al., "Chromatographic and Electrophoretic Investigation of the Properties of Unprotected Low-Sulphur Wool Kerateins", Journal of Chromatography, vol. 405, p. 365-370, 1987.

Pavlath, Attila E., et al., "Clarity of Films fro Wool Keratin", Textile Res. J. vol. 69, No. 7 pp. 539-541, 1999.

Platt, A.J., et al., "A Comparative Study of Silicone Net Dressing and Paraffin Gauze Dressing in Skin-Grafted Sites", Burns, vol. 22, No. 7, pp. 543-545, 1996.

Valenta, Claudia, et al., "The Use of Polymers for Dermal and Transdermal Delivery", European Journal of Pharmaceutics and Biopharmaceutics, vol. 58, pp. 279-289, 2004.

Jonkman, Marcel F., et al., "New Method to Assess the Water Vapour Permeance of Wound Coverings", Biomaterials, vol. 9, pp. 263-267, May 1988.

Ming Yang, Jen, et al., "Properties of Chitosan Containing PP-g-AA-g-NIPAAm Bigraft Nonwoven Fabric for Wound Dressing", Journal of Membrane Science, vol. 243, pp. 1-7, 2004.

Freedman, Gordon, et al., "Practical Treatment of Pain in Patients with Chronic Wounds: Pathogenesis-Guided Management", The American Journal of Surgery, vol. 188, pp. 31S-35S, 2004.

Coderch, L., et al., "Chromatographic Characterization of Internal Polar Lipids from Wool", JAOCS, vol. 72, No. 6, pp. 715-720, 1995.

Coderch, L., et al., "Physicochemical Characteristics of Liposomes Formed with Internal Wool Lipids", JAOCS, vol. 73, No. 12, pp. 1713-1718, 1996.

Wertz, Philip W., et al., "The Composition of the Ceremides from Human Stratum Corneum and from Comedones", The Journal of Investigative Dermatology, vol. 84, No. 5, pp. 410-412, 1985.

Matsumoto, Kiyoichi, et al., "Studies on Regenerated Protein Fibers, III. Production of Regenerated Silk Fibroin Fiber by the Self-Dialyzing Wet Spinning Method", Journal of Applied Polymer Science, vol. 60, pp. 503-511, 1996.

Yang, Yiqi, et al., "Formaldehyde-Free Zein Fiber-Preparation and Investigation", Journal of Applied Polymer Science, vol. 59, pp. 433-441, 1996.

Cates, David M., et al., "Preparation and Properties of Fibers Containing Mixed Polymers III. Polyacrylonitrile-Silk Fibers", Journal of Polymer Science, vol. 21, No. 97, pp. 125-138, 1956.

Schimpf, Warren C., "Fibers from Regenerated Collagen", Ind. Eng. Chem., Prod. Res. Dev., vol. 16, No. 1, pp. 90-92, 1977.

Sastry, T.P., et al., "Graft Copolymerization of Feather Keratin Hydrolyzate: Preparation and Characterization", Journal of Polymer Materials, vol. 14, No. 2, pp. 177-181, 1997.

Tanabe, Toshizumi, et al., "Preparation and Characterization of Keratin-Chitosan Composition Film", Biomaterials, vol. 23, pp. 817-825, 2002.

Marshall, R.C., et al., "Structure and Biochemistry of Mammalian Hard Keratin", Eletron Microsc. Rev., vol. 4, pp. 47-83, 1991. Journal of Applied Polymer Science, vol. 91, pp. 756-762, 2004.

Gillespie, J.M., et al., "Variability in the Proteins of Wool and Hair", Division of Protein Chemistry, CSIRO, vol. 2, pp. 67-77, 1980.

Milgram, Norton W., et al., "Landmark Discrimination Learning in the Dog: Efffects of Age, an Antioxidant Fortified Food, and Cognitive Strategy", Neuroscience and Biobehavioral Reviews, vol. 26, pp. 679-695, 2002.

Yamauchi, Kiyoshi, et al., "Cultivation of Fibroblast Cells on Keratin-Coated Substrata", J. Biomater Sci. Polymer Edn., vol. 9, No. 3, pp. 259-270, 1998.

Braverman, E.R., et al., "The Healing Nutrients Within: Facts, Findings, and New Research on Amino Acids", Basic Health Publications, Inc. (Reference #24 on the Bibliography of the attached document).

Gillespie, J. Morton, "The Structural Proteins of Hair: Isolation, Characterization, and Regulation of Biosynthesis", Biochemistry and Physiology of the Skin, pp. 475-510, 1983.

Kazunori, Katoh, et al., "Preparation and Properties of Keratin-Poly(vinyl alcohol) Blend Fiber", Journal of Appled Polymer Science, vol. 91, pp. 756-762, 2004.

Gorman, Jessica, "Materials Take Wing: What to Do With 4 Billion Pounds of Feathers?" Science News, Feb. 23, 2002, vol. 161, p. 120(2).

* cited by examiner

POROUS KERATIN CONSTRUCT AND METHOD OF MAKING THE SAME

This application claims the benefit of priority of provisional application No. 60/874,010, filed Dec. 11, 2006 and provisional application No. 60/924,032, filed Apr. 27, 2007.

FIELD OF THE INVENTION

The present invention is related to a porous keratin construct, and more specifically, to a range of porous keratin constructs having varying rates of bio-absorbability in a wound. The rate of bio-absorbability of the porous keratin constructs in a wound is altered by controlling the degree of disulfide cross-linking between the keratin proteins in the porous keratin construct. The present invention is also directed to the method of making the porous keratin construct.

BACKGROUND OF THE INVENTION

Chronic wounds can be caused by a variety of events, including surgery, prolonged bed rest, and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers), and venous stasis disease, which can cause full thickness ulcers of the lower extremities. Full thickness wounds tend to heal very slowly. Proper wound care technique, including the use of wound dressings, is extremely important to successful chronic wound management. Chronic wounds affect an estimated four million people a year, resulting in health care costs in the billions of dollars.

The wound healing process involves a complex series of biological interactions at the cellular level, which can be grouped into three phases: hemostasis and inflammation, granulation tissue formation and reepithelization, and remodeling. Keratinocytes (epidermal cells that manufacture and contain keratin) migrate from wound edges to cover the wound. Growth factors such as transforming growth factor-β (TGF-β) play a critical role in stimulating the migration process. The migration occurs optimally under the cover of a moist layer.

Keratin proteins are present in a wide range of biological tissue, performing a structural role in skin, hair and other materials. Keratins extracted from hair have been shown to be a valuable component in wound dressings. Specifically, keratins have been found to be necessary for the reepithelization phase of the wound healing process.

Many wound dressings previously described require that the wound dressing be removed from the open wound after a certain time to be replaced by a new wound dressing because the wound dressing is no longer aiding the healing process, but remains on the wound. In wound dressings such as these, the wound dressing may become attached to the wound due to ingrowth of tissue into the wound dressing, and therefore removal of the wound dressing will re-traumatize the wound and inhibit the healing process.

Other previously described wound dressings comprising keratin have also failed to adequately treat chronic wounds because of an inability to maintain keratin in the wound for a period of time that allows the keratin to promote wound healing. Previously known wound dressings have attempted to use untreated soluble keratin as a component of the wound dressing. However, the untreated soluble keratin is absorbed too quickly and does not stay in the wound long enough to be used in the healing process, and therefore is ineffective in promoting wound healing.

Alternatively, previously described wound dressings comprising insoluble keratin have also failed to adequately treat chronic wounds. Insoluble keratins in wound dressing are not metabolized by the wound and therefore need to be removed from the wound. Removal of the insoluble keratin runs the risk of re-traumatizing the wound as discussed previously and therefore slows or sets-back the healing process. Furthermore, insoluble keratins do not posses the appropriate three-dimensional structure necessary to support maximum cell growth and proliferation. Thus, wound dressings comprising insoluble keratin protein fall short of adequately promoting wound healing.

Previously described wound dressings comprising keratin have also failed to adequately protect against oxidative stress in a wound environment. Sulfhydryl groups are vital in maintaining the oxidant-antioxidant balance within a cell and preventing situations of oxidative stress. However, no previously described wound dressings comprising keratin promote species such as glutathione to combat oxidative stress.

SUMMARY OF THE INVENTION

Keratin has been shown to be a valuable component in wound healing materials. However, to date, no prior art has disclosed a satisfactory manner for effectively introducing keratin into a wound site while still achieving desirable characteristics associated with a wound healing material.

It has been discovered by the inventors of the present application that a porous keratin construct having a controlled degree of disulfide crosslinking between keratin proteins provides a wound healing material with a controlled rate of absorption of the material into the wound. For example, more highly disulfide crosslinked material is maintained in the wound for a relatively longer period of time because of an associated slower rate of bio-absorption of the material into the wound. Conversely, a minimally crosslinked material is maintained in the wound for a relatively sort period of time because of an associated faster rate of bio-absorption of the material into the wound. By controlling the rate of absorption of the wound dressing through controlling the crosslinking in the porous keratin construct, the invention described herein can ensure that keratin remains in the wound for a period of time adequate to aid in the healing of the wound and also reduce or eliminate the need to remove the material from the wound, thus greatly reducing the chance of re-traumatizing the wound site when a new material needs to be applied to the wound.

More specifically, it has been discovered that a porous keratin construct comprising keratin fractions and/or intact keratin, wherein the degree of disulfide crosslinking between keratin protein in the construct is controlled through chemical treatment, such as through treatment with a reducing agent, provides a material that achieves the characteristics of a desirable wound dressing. The intact keratin or keratin fraction may further be S-sulfonated.

The first embodiment of the present invention is directed to a porous keratin construct comprising keratin protein having a predetermined degree of cross-linking between sulfur atoms, wherein the rate at which the porous keratin construct bioabsorbs into a wound is controlled by the predetermined number of re-formed disulfide bonds controls.

In one aspect of the first embodiment, the keratin component used to provide the porous keratin construct is a keratin protein fraction. In another aspect of the first embodiment, the keratin protein component is intact. In still another aspect of the first embodiment, an intact keratin protein fraction is used to provide the porous keratin construct. In a preferred embodiment, the keratin protein fraction may be intermediate filament keratin protein, high sulfur keratin protein or high glycine high tyrosine keratin protein.

In one aspect of the first embodiment, the keratin fraction used to provide the porous keratin construct is s-sulfonated keratin protein fraction, which is a soluble keratin protein.

In another aspect of the first embodiment, the degree of disulfide cross-linking between keratin molecules of the construct is from 5 to 75%, more preferably from 10 to 15%, and most preferably 12%.

In another aspect of the first embodiment, the thickness of the porous keratin construct is from 0.05 mm to 100 mm, more preferably 1 to 3 mm, and most preferably 1.5 mm.

In yet another aspect of the first embodiment, the porous keratin construct is capable of being completely absorbed into the wound.

In another aspect of the first embodiment, the porous keratin construct has a degree of crosslinking such that the porous keratin construct is completely absorbed into the wound after 7 days.

The second embodiment of the present invention is directed to a method for preparing a porous keratin construct. The porous keratin constructs prepared from the preferred method are suitable for use in a wound as a wound healing material. In the method, keratin proteins are dissolved in water to form a solution. The solution is cast and frozen to form a frozen solution. The frozen solution is dried to remove moisture and then chemically treated using a reducing agent, e.g., ammonium thioglycollate. An additional freezing and drying step is performed. Additional steps may be performed to result in a desired form of the porous keratin construct.

In one aspect of the second embodiment, the keratin used in the method is a keratin protein fraction. In another aspect of the second embodiment, the keratin protein is intact. In still another aspect of the second embodiment, an intact keratin protein fraction is used in the method. In a preferred embodiment, the keratin protein fraction may be intermediate filament keratin protein, high sulfur keratin protein or high glycine high tyrosine keratin protein.

In one aspect of the second embodiment, the keratin protein fraction is S-sulfonated keratin protein fraction, which is a soluble keratin protein.

In another aspect of the second embodiment, the plasticizers may include triglycerides, polyol, glycol, polyethers monomers, epoxy monomers and various vegetable oils, which soften and impart flexibility to the keratin construct. In a preferred aspect, the plasticizer is glycerol.

In another aspect of the second embodiment, the step of dissolving the keratin in water takes from 2 to 3 hours.

In still another aspect of the second embodiment, the solution is cast on inert Petri dishes.

In yet another aspect of the inventive method, the freezing steps comprise reducing the temperature of the solution or material to less than −18° C. and the drying steps provide a material with less than 0.6 water activity. The drying steps may also be freeze drying steps in another aspect of the second embodiment.

In still another aspect of the second embodiment, the step of porous keratin construct may be compressed to form a porous keratin sheet having a thickness of from 0.05 mm and 100 mm, more preferably to between 1 mm and 3 mm, and most preferably to 1.5 mm.

In another aspect of the second embodiment, the reducing agent used is a thiol, cysteamine or sulphite, and is preferably ammonium thioglycollate.

DETAILED DESCRIPTION OF THE PREFERRED EMBODIMENTS

Figure 1:
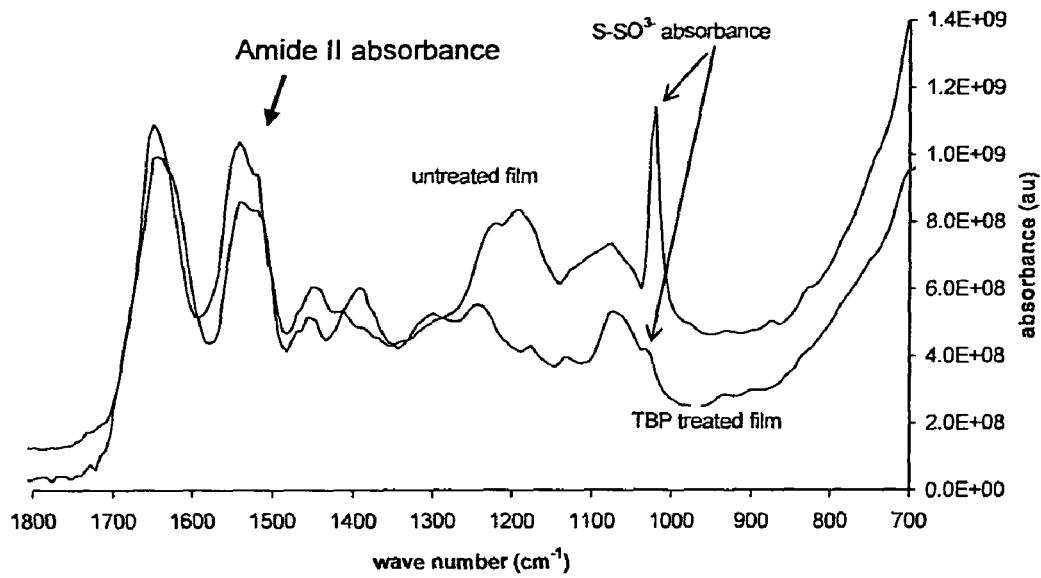
FIG. 1 illustrates an FTIR profile of keratin materials.

The first embodiment of the present invention is directed to a porous keratin construct comprising keratin protein having a predetermined degree of cross-linking between sulfur atoms, wherein the rate at which the porous keratin construct bioabsorbs into a wound is controlled by the predetermined number of re-formed disulfide bonds controls.

A construct as used in the instant application refers to any suitable predominantly solid form for use in a wound-healing application, such as a film, sheet, pad, matrix, screen, block or foam.

Bioabsorption refers to the ability of the material to be absorbed by and into the body.

Keratin is a family of proteins characterized by a high degree of the amino acid cystine, which imparts a high degree of crosslinking to keratin proteins through disulfide links. In the present invention, the number of these disulfide links is controlled in order to control the rate of absorption of the construct into the wound.

The keratin protein of the first embodiment is preferably a keratin protein fraction. Keratin protein fractions are distinct groups from within the keratin protein family, and include intermediate filament proteins, high sulfur proteins and high glycine-tyrosine proteins known in the art.

Intermediate filament proteins are described in detail by Orwin et al. (*Structure and Biochemistry of Mammalian Hard Keratin*, Electron Microscopy Reviews, 4, 47, 1991) and also referred to as low sulfur proteins by Gilliespie (Biochemistry and physiology of the skin, vol. 1, Ed. Goldsmith Oxford University Press, London, 1983, pp. 475-510). Key characteristics of intermediate filament protein family are molecular weight in the range 40-60 kD and a cysteine content (measured as half cystine) of around 4%.

The high sulfur protein family is also well described by Orwin and Gillispie in the same publications referenced above. This protein family has a large degree of heterogeity, but can be characterized as having a molecular weight in the range 10-30 kD and a cysteine content of greater than 10%. A subset of this family is the ultrahigh sulfur proteins, which can have a cysteine content of up to 34%.

The high glycine-tryosine protein family is also well described by Orwin and Gillispie in the same publications referenced above. This family is also referred to as the high tyrosine proteins and has characteristics of a molecular weight less than 10 kD, a tyrosine content typically greater than 10% and a glycine content typically greater than 20%.

For the purpose of this invention, a "keratin protein fraction" is a purified form of keratin that contains predominantly, although not entirely, one distinct protein group as described above.

The keratin protein of the first embodiment may also be intact. The term intact refers to proteins that have not been significantly hydrolyzed, with hydrolysis being defined as the cleavage of bonds through the addition of water. Gillispie considers intact to refer to proteins in the keratinized polymeric state and further refers to polypeptide subunits which complex to form intact keratin in wool and hair. For purposes of this invention, intact refers to the polypeptide subunits described in Gillispie. These are equivalent to the keratin proteins in their native form without the disulfide crosslinks formed through the process of keratinization.

Intact keratin proteins and keratin protein fractions are discussed in greater detail in co-pending U.S. patent application Ser. No. 10/583,445, filed Jun. 19, 2006 and of which the entire application is hereby incorporated by reference.

In a preferred aspect of the first embodiment, the keratin of the porous keratin construct is S-sulfonated keratin protein. S-sulfonated keratin refers to keratin protein that undergoes a process wherein the disulfide bonds between cystine amino acid in keratin protein are reversibly modified to create polar functional groups that allow for controlled re-introduction of the natural disulfide crosslinks originally present in the keratin protein. S-sulfonated keratins have cysteine/cystine present predominantly in the form of S-sulfocysteine. This highly polar group imparts a degree of solubility to proteins. Whilst being stable in solution, the S-sulfo group is a liable cysteine derivative, highly reactive towards thiols, such as cysteine, and other reducing agents. Reaction with reducing agents leads to conversion of the S-sulfo cysteine group back to cystine. S-sulfo cysteine is chemically different from cysteic acid, although both groups contain the $SO_3^-$ group. Cysteic acid is produced irreversibly by the oxidation of cysteine or cystine and once formed cannot form disulfide crosslinks back to cysteine. S-sulfocysteine is reactive towards cysteine and readily forms disulfide crosslinks.

In the case of S-sulfonated keratin protein, the conversion of the S-sulfonate form to the crosslinked disulfide form may be accomplished through application of reducing conditions, for example, by applying a thiol. The reducing agent may be any suitable keratin reducing agent, including thiols, such as cysteine, thioglycolic acid, thiolactic acid, slats thereof and esters thereof, cysteamine and its salts, and sulphites.

S-sulfonated keratin protein may be prepared by a variety of methods, including those described in NZ/PCT02/00125, incorporated herein by reference.

The mechanism for modifying the cystine disulfide bond to cysteine S-sulfonate is summarized as follows, wherein K is keratin:

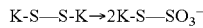

$$K\text{-}S\text{-}S\text{-}K \rightarrow 2K\text{-}S\text{-}SO_3^-$$

The mechanism for reforming the crosslinks may be summarized as follows, wherein K is keratin and R is a reducing agent:

$$K\text{-}S\text{-}SO_3^- + R\text{-}S^- \rightarrow K\text{-}S\text{-}S\text{-}R + SO_3^{2-}$$

$$K\text{-}S\text{-}S\text{-}R + R\text{-}S^- \rightarrow K\text{-}S^- + R\text{-}S\text{-}S\text{-}R$$

$$K\text{-}S\text{-}SO_3^- + K\text{-}S^- \rightarrow K\text{-}S\text{-}S\text{-}K + SO_3^{2-}$$

Cross-linking as used in the instant application refers to the sulfur-sulfur bond formed between amino acids of adjoining keratin molecules. Controlling the amount of disulfide crosslinks allows for control of solubility and rate of biodegradation due to the fact that the disulfide crosslinks are less susceptible to enzymatic hydrolysis than peptide bonds.

The degree of cross-linking as used in the instant application is a measurement expressing the proportion of $S\text{-}SO_3^-$ functional groups that have been removed from the keratin construct and reconverted to disulfide bonds (i.e., cross-linked), according the to equation above. This may be determined by measuring the absorbance of the $S\text{-}SO_3^-$ chemical group in the IR spectrum. It has been assumed that removal of the $S\text{-}SO_3^-$ absorbance leads directly to a disulfide crosslink according to the mechanism above, and therefore less $S\text{-}SO_3^-$ absorbance equates to more crosslinking. An FTIR profile of keratin materials is presented in FIG. 1.

Materials crosslinked to different extents have been measured relative to the standard amide II protein absorbance. On this basis, a percentage has been allocated to the degree of crosslinking occurring in the keratin construct, as detailed in Table 1. For the experimental data given in Table 1, the data point for 15 minutes crosslinking treatment time is assumed to be an outlier.

TABLE 1

% disulfide content as determined by FTIR measurement of peak intensity.

| Crosslinking Treatment Time (mins) | Ratio of $SSO_3^-$ to amide II | % disulfide crosslink |
|---|---|---|
| 0 | 1.09 | 0 |
| 10 | 0.96 | 12 |
| 15 | 0.56 | 49 |
| 20 | 0.64 | 41 |
| 30 | 0.56 | 49 |
| 45 | 0.31 | 72 |
| 60 | 0.27 | 75 |

The degree of disulfide crosslinking in the porous keratin construct of the present invention is controlled in order to control the rate of absorption of the construct into the wound. Therefore, the degree of disulfide crosslinking in the porous keratin construct of the present invention may be any suitable amount necessary to achieve a desired rate of bio-absorption into the wound. The degree of disulfide crosslinking is preferably 5 to 75%, more preferably 10 to 15%, and most preferably 12%. If the degree of crosslinking is too high, the material will absorb into the wound too slowly because the material will remain in the wound despite no longer aiding in healing. Removal of the material will be required, which presents the risk of re-traumatizing the wound if the skin has grown into the porous material. If the degree of crosslinking is too low, the material will absorb into the wound too quickly. Thus, the keratin in the material will not be present at the wound site for a sufficient enough period of time to help improve and enhance wound healing.

Disulfide cross-linking may be controlled by controlling the amount of time the construct is treated with reducing agent used in the process of preparing the porous keratin construct of the present invention. The relationship between the amount of time treated with reducing agent and the amount of cross-linking is generally a monotonically increasing relationship, i.e., the more time the construct is treated with reducing agent, the more cross-linking occurs. This is broadly substantiated by the experimental data shown in Table 1. As noted above, the data point for 15 minutes crosslinking treatment is assumed to be an outlier.

As discussed above, more crosslinking will allow the construct to remain in the wound for a longer period of time. For example, as explained in further detail below, it has been determined that treating the construct with a reducing agent for 10 minutes will lead to approximately 12% crosslinking, and will cause the construct to absorb into the wound in one week. A shorter treatment time will lead to a lower crosslinking percentage and a faster rate of absorption into the wound. A longer treatment time will lead to a higher crosslinking percentage and a slower rate of absorption into the wound. This relationship is exemplified in Example II, discussed below.

The porous keratin construct is also capable of protecting against oxidative stress. Keratin proteins are characteristically rich in the sulfur amino acid cystine, and are one of the richest natural resources of cystine available. Cystine is readily converted to cysteine under reducing conditions. Cysteine has antioxidant capacity similar to that of glutathione, with reduction potentials of −230 mV and −240 mV, respectively. As a source of sulfur rich amino acids, keratin can act as an antioxidant. Furthermore, by providing essential components for the biochemical synthesis of glutathione (cystine, glutamic acid and glycine), keratin can influence important antioxidant pathways in the body.

Conventional methods for isolating keratin from natural resources involve hydrolysis using acid, alkali or enzymatic conditions. This typically results in substantial degradation to the protein, and the resulting peptides are typically significantly lower in cystine content than their source keratin. For example, cystine can be irreversibly degraded to form cysteic acid or lanthionine under acid or alkaline conditions. Intact proteins that are not hydrolyzed maintain their cysteine content, and so are a preferred source of keratin for ingestion and can play a more active role in the effect redox related pathways in the body.

S-sulfo cysteine is a derivative of cysteine that provides reversible modification to the cysteine group. This prevents the oxidation of two neighboring cysteine species to form cystine, whilst still maintaining the reactivity towards oxidants. This is demonstrated by the antioxidant capacity of s-sulfo keratin derivative used in the construct of the present invention.

Keratin protein fractions can have a higher individual content of cystine than the source keratin, and are advantageous when used to affect the body's redox pathways. For example, the high sulfur protein fraction HSP can have a cystine content of up to 22 mol %. Intact keratin protein fractions such as the ones used in the construct of the instant application can benefit a range of health conditions, including those linked to redox pathways, and have been linked to some benefits associated with cysteine, N-acetyl cysteine (NAC) or glutathione supplementation. This is discussed in greater detail in co-pending U.S. patent application Ser. No. 11/370,063, filed Mar. 8, 2006 and of which the entire application is hereby incorporated by reference.

The construct comprising keratin may be of any shape or cross section suitable for use in wound care application. For example, the construct may be cut into any number of shapes and sizes, depending on the size and shape of the wound.

The thickness of the keratin construct may be any thickness appropriate for use in wound healing, for example, 0.01 mm to 100 mm, preferably 0.05 mm to 5 mm, more preferably 1 to 3 mm, and most preferably 1.5 mm. The preferred ranges of thickness ensure that the density of the construct, the flexibility of the construct and the rate of bioabsorption of the construct is appropriate for use on a patient. In other words, the preferred thickness of the construct is such that the construct is thick enough so as to be firm and robust and prevent the construct from breaking apart when it is handled or placed on the wound. However, the preferred thickness of the construct is also such that the construct is not so thick so as to inhibit movement of the dressing with wound area (e.g., when the wound is on a joint, the construct should have a thickness that allows it to be flexible enough to move with movement of the joint). The preferred ranges of thickness help to ensure that the patient does not find the porous keratin construct uncomfortable when worn on the wound.

The keratin construct described herein is porous. While the exact porosity and pore size of the construct may vary, the pores of the keratin construct sheet are interconnected. The interconnected pores serve as an important feature for promoting cell growth in the wound area. The porous keratin construct is also naturally adhesive because of the porous structure. The porous structure allows for ingrowth of exudates.

It is believed that the porous keratin construct described herein may be completely absorbed into the wound over time to support growth of epithelial tissue. In this manner, there is no need to remove a construct from the site. Consequently, the potential for re-traumatizing a wound site when tissue has grown into a construct that needs to be removed is avoided.

By completely absorbed into the wound it is meant that a substantial portion of the construct has been absorbed into the wound such that there is no visible portion of the porous keratin construct remaining in the wound that may be extracted from the wound. The time for which it takes the porous keratin construct to completely absorb into the wound may be any time suitable for wound healing. Preliminary investigation has revealed that it would be most convenient for the construct to completely absorb within 7 days, which corresponds to approximately 12% cross-linking.

In addition to being used as, e.g., a stand alone wound dressing, the keratin construct of the first embodiment is also useful in negative pressure therapy. Negative pressure therapy (or vacuum induced healing) generally comprises creating a seal around a wound by adhering an impermeable sheet to the skin surrounding the wound, connecting a means for supplying negative pressure to the area under the impermeable sheet, and then applying negative pressure to the area under the sheet. Applying negative pressure to a wound in this manner has been found to promote the migration toward the wound of epithelial and subcutaneous tissues, as well as causing a mechanical-like contraction of the wound with simultaneous removal of excess fluid. In this manner, negative pressure therapy augments the body's natural inflammatory process while alleviating many of the known intrinsic side effects.

U.S. Pat. No. 4,969,880 issued on Nov. 13, 1990 to Zamierowski generally describes negative pressure therapy and apparatus associated therewith. As disclosed in the '880 patent, negative pressure therapy generally requires that a foam pad be placed in the wound bed prior to covering the wound area with an impermeable sheet and applying negative pressure. The foam pad serves to evenly distribute the negative pressure to the wound as well as to keep the impermeable sheet from collapsing into the wound.

Accordingly, the porous keratin construct of the first embodiment may be employed as the foam pad used in negative pressure therapy. Use of the keratin construct of the first embodiment in negative pressure therapy is advantageous in that the keratin material is bioabsorbable and is therefore less likely to adhere to the wound due to ingrowth of tissue into the keratin construct as compared to when synthetic material is used for the pad. As discussed above, avoiding ingrowth of tissue into the wound dressing is desirable so as to avoid retraumitizing a wound upon removal from the wound bed.

In the second embodiment of the instant invention, a method for forming a porous keratin construct comprising keratin is disclosed. The method comprises a) dissolving keratin protein in water to form a solution; b) casting the solution of step a); c) freezing the solution of step b) to form a frozen solution; d) drying the frozen solution of step c) to form a porous foam; e) adding reductant to the foam of step d)

to form a soft matrix; and f) freezing and drying the soft matrix of step e) to form a porous keratin construct.

In a preferred aspect of the second embodiment, the keratin protein is keratin protein fraction as described above with respect to the first embodiment. The keratin may also preferably be intact as described above with respect to the first embodiment. More preferably, the intact keratin protein fraction is selected from the group consisting of intermediate filament protein, high sulfur protein and high glycine-tyrosine protein as described above with respect to the first embodiment. In a most preferred aspect of the second embodiment, the intact keratin protein fraction is S-sulfonated as described previously.

In another aspect of the present invention, the keratin protein is dissolved in water for a time period of 2 to 3 hours in order to ensure near-complete dissolution of the keratin in water.

In still another aspect of the second embodiment, a plasticizer is added during the dissolution step and the reducing agent step in order to impart softness and flexibility to the porous keratin construct. The addition of plasticizer makes the resulting porous keratin construct more comfortable to the recipient because the keratin construct becomes more flexible and soft. The plasticizer may be any suitable plasticizer for use in a porous keratin construct, and is preferably polyalcohol and more preferably glycerol.

A pH regulator may also be added during the dissolution step in order to neutralize the solution. The pH regulator may be any pH regulator suitable for neutralizing a keratin powder in solution, and is preferably caustic soda.

By casting it is meant pouring into a mold to obtain a desired shape or a sheet. The size of the cast shape or sheet is not limited, and a large shape or sheet produced from the method may be cut up in a later step to create smaller shapes or sheets. In still another aspect of the second embodiment, the solution is cast onto an inert Petri dish.

In a preferred aspect of the second embodiment, drying steps d) and g) are freeze drying steps. By freeze drying it is meant drying in a high vacuum. In one aspect of the second embodiment, the process of freeze drying is carried out to obtain a porous foam having less than 0.6 water activity. Water activity is the relative availability of water in a substance. It is defined as the vapor pressure of water divided by that of pure water at the same temperature.

The step of freezing the solution and freezing the soft matrix preferably reduces the temperature of the solution to less than −18EC.

In a preferred method of forming a porous keratin construct with a controlled amount of disulfide crosslinking, the reducing agent used is ammonium thioglycollate. This reagent is catalytic in the process and entirely removed following the reaction by washing extensively with water, as is residual sulfite displaced during the crosslinking.

In a preferred aspect of the second embodiment, the foam of step d) is treated with the reductant in step e) for 1 to 60 minutes, and more preferably is treated with reductant for 10 minutes.

In a preferred aspect of the second embodiment, the porous keratin construct may be further processed into a desirable form, such a film, sheet, matrix or foam. When constructing a sheet, a compression step is performed to reduce the thickness of the porous keratin construct to a thickness that makes a sheet that is easy to handle and comfortable to a recipient. Specifically, the preferred range of 0.05 mm to 5 mm, more preferred range of 1 to 3 mm, and the most preferred thickness of 1.5 mm ensures that the sheet is not so thin and brittle so as to fall apart when being handled, but ensures that the sheet is not so thick as to not be flexible when placed on the wound. Any additional processing steps capable of creating a foam, matrix, film or the like may be performed on the porous keratin construct.

Example I

A method of preparing porous keratin sheets according an embodiment of the present invention was performed according to the following steps:

1. Dissolve and neutralize the S-sulfonated keratin powder and add additives—The keratin powder was dissolved in water to produce a solution with total solids of 5-8%. Caustic Soda was used to neutralize the acidic powder to pH 7.0-7.5. Glycerol was added to the solution as a plasticizer. The mass fraction of glycerol in the final solution was 2%. The dissolving process step took place over 2-3 hours.

2. Filtration—The solution was filtered through a 50 micron wedgewire filter. The retentate in the filter comprised <2% of the solids added at step 1.

3. Casting—The solution was cast on inert, non-contaminating, single-use, polystyrene Petri dishes. The square Petri dishes were 100 mm×100 mm.

4. Freezing—The solution on the Petri dish was placed in a freeze-in-place freeze dryer. The Petri dish was left 2 hrs in the freezer and the material's temperature fell below −18° C.

5. Drying—The frozen material was dried at 20 Pa (abs) pressure and 35 C for 16 hours. A porous foam with a water activity of <0.6 was produced.

6. Treatment—A reducing solution of ammonium thioglycollate (0.25M at 7.4 pH with 0.1M phosphate buffer) was added to the foam for 10 minutes and washed with water 8 times to remove the residues of the ATG. During the eighth wash, 10% glycerol was added to the solution as a plasticizer. A soft matrix was produced.

7. Freezing—The soft matrix was placed on a 120 mm×120 mm Petri dish and placed in a freeze-in-place freeze dryer. The material in the Petri dish was allowed to fall below −18° C.

8. Drying—The frozen material was dried at 20 Pa (abs) pressure and 35 C for 16 hours. A porous construct with a water activity of <0.6 was produced.

9. Compressing—The porous construct was run through a press to reduce the thickness of the construct from 5 mm to 1.5 mm.

Example II

The effect of disulfide crosslinking on the rate of degradation in vitro of S-sulfonated keratin constructs produced by the method of the present invention is illustrated in the following experiment. The results of the in vitro study correlate to the results expected when studying absorption of the construct into a wound.

The extent of keratin loss from porous keratin constructs produced by the method of present invention is summarized below. The porous keratin constructs were treated with a solution of ammonium thioglycollate (0.25M $NH_4$thioglycollate, 0.1 M phosphate buffer to pH 7) for the length of time indicated. Enzyme was used to simulate the activity of the wound absorbing the material. The enzyme level was 0.5 mg/mL (Trypsin 1800 BAEE units/mg) in 0.05 mol/L TRIS buffer.

TABLE 2

% keratin lost in varying samples of keratin construct according to the present invention.

| Time/ days | control | 10 mins xl | 20 mins xl | 30 mins xl | 45 mins xl | 60 mins xl |
|---|---|---|---|---|---|---|
| 0.25 | 94.47 | 83.43 | 63.22 | 56.07 | 68.03 | 53.55 |
| 1 | 94.89 | 94.53 | 76.55 | 81.11 | 80.23 | 76.62 |
| 2 | 100.00 | 95.41 | 89.86 | 82.21 | 89.44 | 77.90 |
| 3 | 100.00 | 74.44 | 90.54 | 82.38 | 93.10 | 87.93 |
| 4 | 100.00 | 93.59 | 56.36 | 60.84 | 78.71 | 89.67 |
| 5 | 100.00 | 97.07 | 73.42 | 59.48 | 71.03 | 67.36 |
| 6 | 100.00 | 95.53 | 71.08 | 65.87 | 78.87 | 69.17 |
| 8 | 100.00 | 93.38 | 70.76 | 77.07 | 84.10 | 68.23 |

Figure 2:
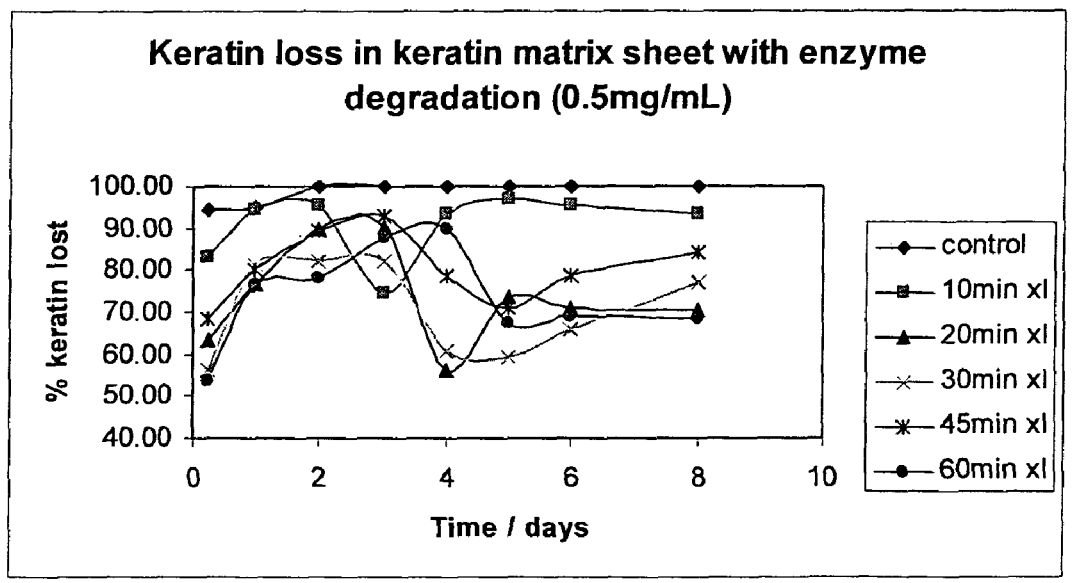
FIG. 2 illustrates the percentage of keratin lost in varying samples of keratin construct according to the present invention.

FIG. 2 and Table 2 show that keratin constructs treated for a longer period of time generally exhibit less keratin loss over a given period of time than keratin constructs treated for shorter periods of time. This is broadly evident from the data presented in FIG. 2 and Table 2, although the data does display noise at various crosslinking treatment durations and time periods.

Example III

An evaluation of keratin dressings in a clinical environment was conducted using a prospective enrollment of a convenience sample at a specialist wound care clinic of patients with venous and mixed arterial-venous chronic lower leg wounds. 22 patients, ranging in age from 42 to 91 years with wounds of duration ranging from 3 months to 22 years, used one of three forms of keratin based dressing for 8-12 weeks. 7 patients commenced treatment with the keratin matrix sheet dressing prepared as per Example 1. All patients continued with their standard secondary dressing. Patient and Specialist wound care nurses completed questionnaires at each dressing change regarding Overall preference, Ease of application, Comfort, Duration of dressing change, Understanding of dressing use, Ability of dressing to stay in place, Satisfaction regarding further use, and Ease of removal. Nurses also completed sections on Ease of access from packaging, Appropriateness of dressing sizes, Choice of dressing sizes, and Ease of handling. The nurses monitored the wound site for any adverse reactions.

The keratin matrix sheet dressing was preferred by patients and nurses relative to their standard dressings. Overall, 82% of patients and 73% of nurses preferred or very much preferred the keratin matrix dressings. 18% of patients and 23% of nurses overall very much preferred the matrix dressings. The matrix dressings were considered easier to apply or remove and compared with other dressings, the matrix dressings were also clearly quicker to change. The matrix dressings were considered comfortable and stayed in place very well.

Wound dressings were changed on a weekly basis. The keratin matrix sheet dressing prepared as per Example I was changed every week. The degree of crosslinking used to prepare the keratin matrix sheet dressing maintained the dressing in the wound such that is was appropriate to apply a further sheet to the wound every week.

Variations

The foregoing description of the invention has been presented describing certain operable and preferred embodiments. It is not intended that the invention should be so limited since variations and modifications will be obvious to those skilled in the art, all of which are within the spirit and scope of the invention.

The invention claimed is:

1. A compressed porous keratin foam having a water activity of less than 0.6 comprising keratin protein, wherein the foam is constructed of disulfide cross-linked soluble keratin proteins, and further wherein the degree of cross-linking is effective to inhibit solubility of the foam such that from about 93% to about 97% of the foam is absorbed when placed in a solution of 0.5 mg/ml trypsin for a period of 5 to 8 days.

2. The compressed porous keratin foam as claimed in claim 1, wherein the keratin protein is a keratin protein fraction.

3. The compressed porous keratin foam as claimed in claim 1, wherein the keratin protein is intact.

4. The compressed porous keratin foam as claimed in claim 2, wherein the keratin protein is intact.

5. The compressed porous keratin foam as claimed in claim 4, wherein the keratin protein fraction is selected from the group consisting of intermediate filament protein, high sulfur protein and high glycine-tyrosine protein.

6. The compressed porous keratin foam as claimed in claim 5, wherein the intact keratin protein is S-sulfonated keratin protein.

7. The compressed porous keratin foam as claimed in claim 1, wherein the degree of cross-linking is from 5 to 75%.

8. The compressed porous keratin foam as claimed in claim 1, wherein the degree of cross-linking is from 10 to 15%.

9. The compressed porous keratin foam as claimed in claim 1, wherein the degree of cross-linking is about 12%.

10. The compressed porous keratin foam as claimed in claim 1, wherein the thickness of the porous keratin construct is from 0.05 mm to 100 mm.

11. The compressed porous keratin foam as claimed in claim 1, wherein the thickness of the porous keratin construct is 1.5 mm.

* * * * *